(12) United States Patent
Graeve

(10) Patent No.: US 9,237,943 B2
(45) Date of Patent: Jan. 19, 2016

(54) BRUSH HEAD ATTACHMENT

(71) Applicant: M+C Schiffer GmbH, Neustadt/Wied (DE)

(72) Inventor: Arndt Graeve, Koblenz (DE)

(73) Assignee: M+C SCHIFFER GMBH, Neustadt/Wied (DE)

( * ) Notice: Subject to any disclaimer, the term of this patent is extended or adjusted under 35 U.S.C. 154(b) by 21 days.

(21) Appl. No.: 14/035,578

(22) Filed: Sep. 24, 2013

(65) Prior Publication Data

US 2015/0082560 A1   Mar. 26, 2015

(51) Int. Cl.
*A61C 17/22* (2006.01)
*A61C 17/34* (2006.01)
*A46B 5/00* (2006.01)
A46B 13/02 (2006.01)

(52) U.S. Cl.
CPC ............. *A61C 17/222* (2013.01); *A46B 5/0095* (2013.01); *A61C 17/3481* (2013.01); *A46B 13/023* (2013.01)

(58) Field of Classification Search
CPC ...... A46B 13/00; A46B 13/02; A46B 13/023; A61C 17/00; A61C 17/16; A61C 17/20; A61C 17/22; A61C 17/222; A61C 17/32; A61C 17/34; A61C 17/3481; A61C 17/3409

USPC .................................... 15/22.1; 433/118–124
See application file for complete search history.

(56)  References Cited

U.S. PATENT DOCUMENTS

2011/0107536 A1* 5/2011 Dabrowski et al. .......... 15/167.1
2012/0182723 A1* 7/2012 Sharrah et al. ................ 362/157

FOREIGN PATENT DOCUMENTS

DE         102011053774     *  3/2013
WO           2009077922 A1     6/2009

* cited by examiner

*Primary Examiner* — Mark Spisich
(74) *Attorney, Agent, or Firm* — The Webb Law Firm

(57)  ABSTRACT

The present invention relates to a brush head attachment, in particular for an electric sonic toothbrush, comprising a shank member carrying a bristle bundle, and a coupling member (1) provided on the fastening-side end of said shank member with at least one connection surface for a drive shaft of said handpiece which, when a brush head attachment is mounted on a handpiece, protrudes into said coupling member (1), a spring element that can be operatively connected with said drive shaft for securing said drive shaft to said brush head attachment and/or transferring a drive motion of said drive shaft to said brush head attachment, and a metal ring (4) disposed in a widened fastening foot (2) formed by said coupling member (1). In this inexpensively manufactured brush head attachment according to the present invention, said metal ring (4) is a die-cast member.

7 Claims, 4 Drawing Sheets

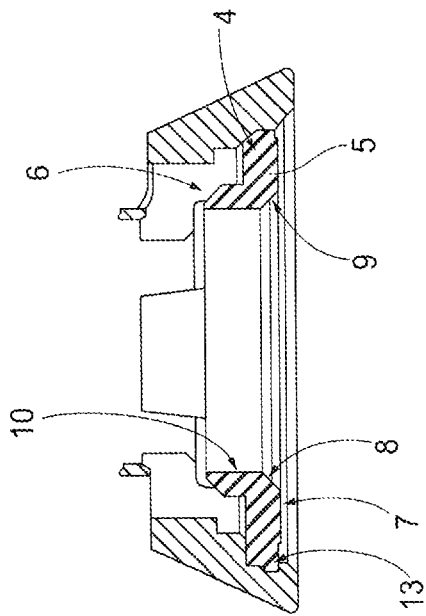
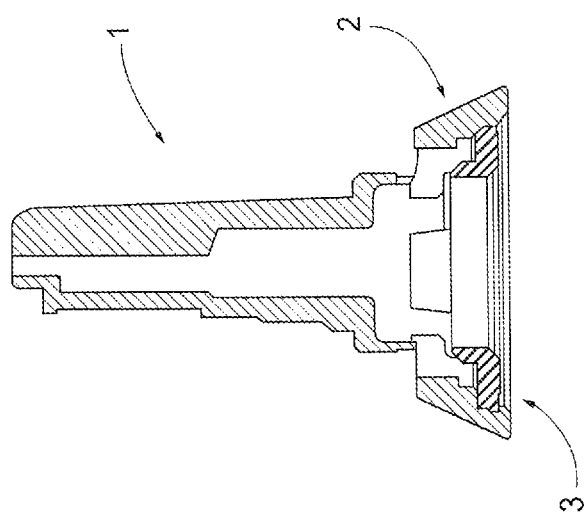
FIG. 4
FIG. 5

BRUSH HEAD ATTACHMENT

BACKGROUND OF THE INVENTION

1. Field of the Invention

The present invention relates to a brush head attachment which can be used with an electric sonic toothbrush.

2. Description of Related Art

Such a brush head attachment with an associated handpiece is known from WO 2009/077922 A1. With this reference, its disclosure content is to be included in the disclosure of the present application, at least to the extent as this relates to the basic structural design of the brush head attachment and the handpiece. The handpiece usually has a power source in the form of a battery or of an accumulator battery and a motor being activatable by a switch exposed on the outer surface of the handpiece and being connected to a drive shaft in order to set the latter into motion.

The brush head attachment of the present invention is in particular an attachment for a sonic, especially an ultrasonic toothbrush, in which the drive shaft is by activation of the motor caused to oscillate preferably in the ultrasonic range. This oscillation is transmitted via the brush head attachment to the bristle bundles.

The shank member carrying the bristle bundles—as is also apparent from WO 2009/077922 A1—at its fastening-side end comprises a bore into which a spring element and a coupling member are introduced. The coupling member forms a widened fastening foot, which usually at the face side bears against the handpiece when the brush head attachment is mounted onto the handpiece. Within the widened fastening foot, a metal ring is provided which in prior art is offset inwardly from the face side created by the coupling member made of plastic. The metal ring forms a mass which improves the oscillation behavior of the shank member, in that the oscillation motion of the drive shaft causes a transfer of the oscillation as directly as possible to the cleaning-side end of the shank member. For this, however, it is necessary to accurately insert the metal ring into the fastening foot and anchor it there without any tolerance.

Nowadays, this metal ring is for this purpose manufactured as a stainless steel ring. A semi-finished stainless steel product is turned to size. This is followed by eroding the semi-finished product. This method is costly. Moreover, it can not always be ruled out that manufacturing-related burrs remain or tolerance limits to be observed are exceeded, respectively. In the production of the brush head attachment, this leads to rejects and production downtime where the metal ring is to be introduced into the injection-molded coupling member and mounted therein.

SUMMARY OF THE INVENTION

In some embodiments, the present invention provides a brush head attachment, in particular for an electric sonic toothbrush, comprising a shank member carrying a bristle bundle, and a coupling member (1) provided on the fastening-side end of said shank member with at least one connection surface for a drive shaft of said handpiece which, when a brush head attachment is mounted on a handpiece, protrudes into said coupling member (1), a spring element that can be operatively connected with said drive shaft for securing said drive shaft to said brush head attachment and/or transferring a drive motion of said drive shaft to said brush head attachment, and a metal ring (4) disposed in a widened fastening foot (2) formed by said coupling member (1), wherein said metal ring (4) is a die-cast member.

In some embodiments, the present invention provides a brush head attachment, in particular for an electric sonic toothbrush, comprising a shank member carrying a bristle bundle, and a coupling member (1) provided on the fastening-side end of said shank member with at least one connection surface for a drive shaft of said handpiece which, when a brush head attachment is mounted on a handpiece, protrudes into said coupling member (1), a spring element that can be operatively connected with said drive shaft for securing said drive shaft to said brush head attachment and/or transferring a drive motion of said drive shaft to said brush head attachment, and a metal ring (4) disposed in a widened fastening foot (2) formed by said coupling member (1), wherein said metal ring (4) is a die-cast member made of zinc forming a flange region (5) from which a pin section (6) extending into said coupling member (1) projects away, and from which a ring surface (7) projects at the opposite side, the outer diameter of which is smaller than the outer diameter of said metal ring (4), wherein said ring surface (7) changes via a phase (9) to a uniform cylindrical inner circumferential surface (10) of said metal ring (4).

BRIEF DESCRIPTION OF THE DRAWINGS

Further details and advantages of the present invention shall become apparent from the following description in combination with the drawings. This drawing is based on the drawings submitted with WO 2009/077922 A1 (incorporated by reference in its entirety) and only shows the coupling member illustrated there in FIGS. 3a, 3b and 5. The remaining components of the embodiments of the brush head including the drive shaft correspond to WO 2009/077922 A1 WO 2009/077922A1 is the publication of PCT/IB08/055168, which entered the US national stage as U.S. application Ser. No. 12/374,871 (issued as U.S. Pat. No. 8,782,841). U.S. application Ser. No. 12/374,871 published as US Patent Applic. Publication. No. 2010/0251493A1. US Patent Applic. Publication No 2010/0251493A1 is incorporated by reference herein in its entirety

FIG. 1 shows a partially exploded view of a toothbrush described herein comprising a handle portion and a brushhead assembly portion FIG. 2 shows an exploded view of the brushhead assembly portion of FIG. 1;

FIG. 4 shows a sectional view through the coupling member with the metal ring; and FIG. 5 shows an enlarged sectional view of only a fastening foot of the coupling member with the metal ring.

DETAILED DESCRIPTION

Figure 1:
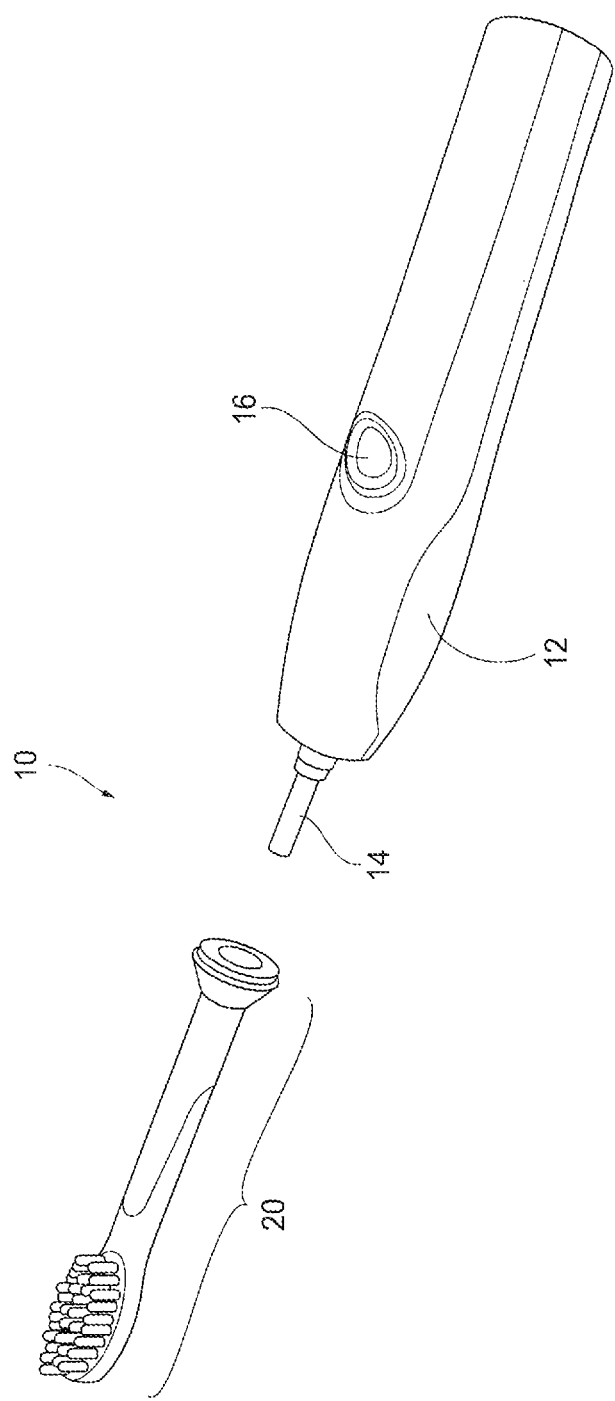
FIG. 1 shows a toothbrush which includes a handle portion with a drive assembly which includes an extending driveshaft 14, the driveshaft driven by a motor (not shown positioned within handle. The motor moves the driveshaft in an oscillating manner through a selected angle. The motor is controlled by a user-operated on/off switch 16. Removably mounted on driveshaft 14 is a brushhead assembly 20.
Figure 2:
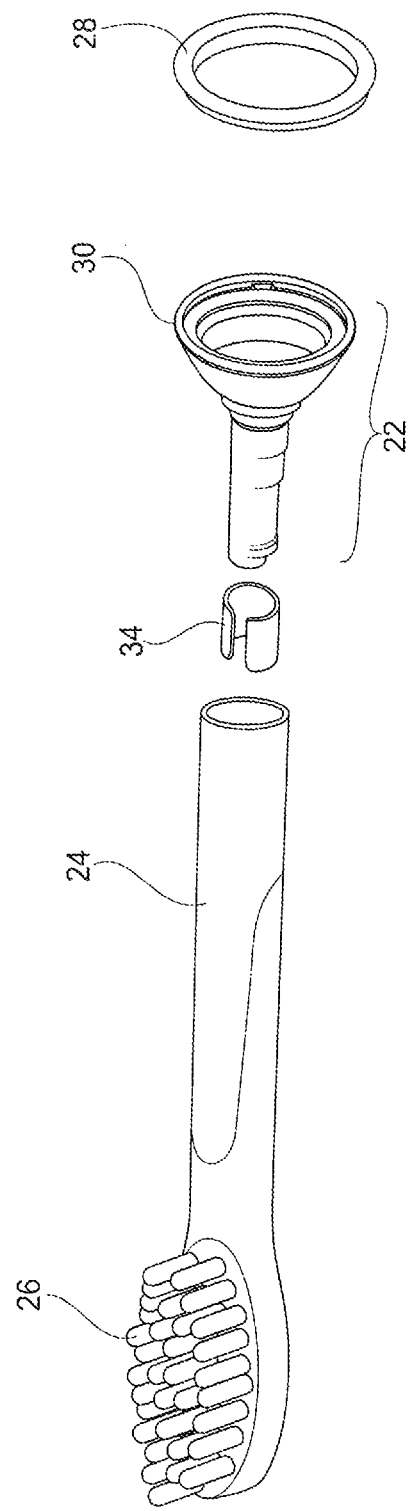
Referring to FIG. 2, the brushhead assembly 20 includes a coupling assembly 22 which fits snugly into and is captured by an arm portion 24 of the brushhead assembly. Positioned on a distal end of the arm portion is a conventional brush member 26 which cleans the teeth. In operation, brush member 26 rotates/oscillates back and forth through a selected angle to accomplish the desired cleansing. The coupling assembly may further include a ring 28 at the proximal end 30 of the coupling assembly. The ring can be different colors to identify the user of the brushhead assembly. The coupling assembly further includes a spring member 34 which fits around a portion of the body of the coupling assembly 22.
Figure 3:
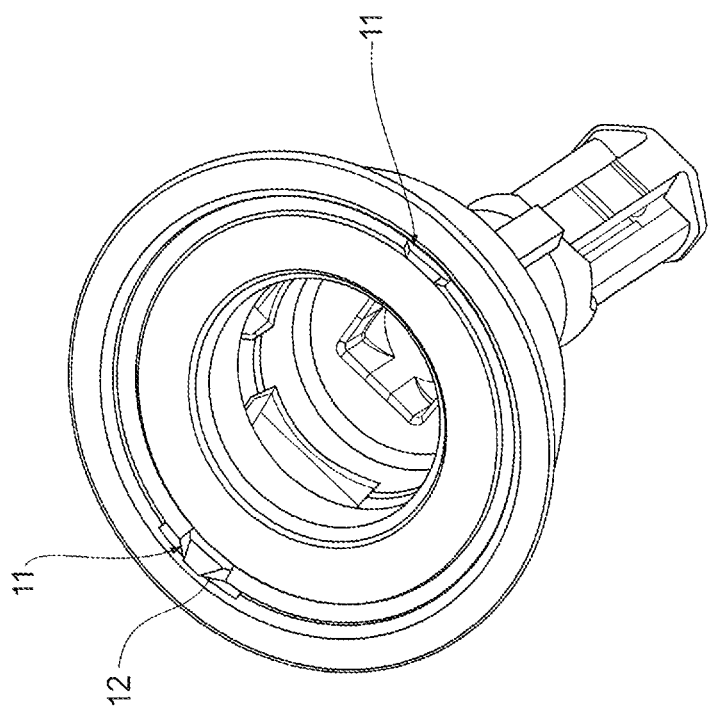
FIG. 3 shows a perspective top view of the bottom side of the embodiment illustrated in FIGS. 1 and 2.

The present invention is based on the problem of proposing a brush head attachment of the aforementioned type which can be manufactured at lower costs without requiring significant changes to existing plastic parts.

To solve this problem, the present invention proposes a brush head attachment having the features of claim 1. It differs from generic prior art in that the metal ring is a die-cast member. The brush head attachment according to the invention provides the advantage that the metal ring as a die-cast member has a shaping final contour so that no geometric deviation from the set target is to be feared. Furthermore, the metal ring can be manufactured at low costs in mass production. Since the metal ring is manufactured into a final shape by casting, the metal ring remains free of burrs.

The metal ring is according to a preferred development of the present invention a die-cast member made of zinc. In view of the lower density of zinc as compared to stainless steel, and in view of the desired mass of the metal ring, the latter, in accordance with a preferred development of the present invention over the metal ring made of stainless steel previously known in prior art, is extensively thickened. For this purpose, the metal ring preferably has a flange portion usually forming the largest diameter of the metal ring and from which a pin section extending into the coupling member projects away. On the side of the metal ring opposite to the pin section, a ring surface protrudes, the external diameter of which is smaller than the outer diameter of the metal ring. This protruding ring surface and the volume bound therein compensate for the difference in density between the stainless steel according to prior art and the die-cast member made of zinc according to the present invention. The ring surface formed by the front face surface of the metal ring is preferably in the axial direction behind a face surface formed by the coupling member, in particular for bearing against the handpiece.

On the inner circumference, the ring surface according to a preferred embodiment of the present invention changes via a phase to a uniform cylindrical inner circumferential surface of the metal ring. Accordingly, the metal ring has only a uniform inner circumferential surface from which said phase comes away at the free end of the metal ring. This phase can directly pass over to the outer surfaces of the metal ring at the face side and formed by the ring surface.

FIG. 4 shows a coupling member 1, which is made of plastic by injection-molding and at its fastening-side end comprises a widened fastening foot 2. The widened fastening foot 2 comprises a recess 3 into which a metal ring 4 is inserted.

The metal ring 4 is a die-cast member made of zinc. The metal ring 4 has a flange region 5, a pin section 6 protruding therefrom in the direction of the coupling member 1, and at a face surface exposed at the coupling member 1 further forms a ring surface 7 by a ring region 8 projecting at the outer circumference of the flange region 5 and having a smaller outer diameter than the flange region 5 and at the inner circumference turning into a phase 9. In the embodiment shown, the ring section protrudes with cylindrical inner and outer circumferential surfaces from the flange region 5. Beyond that, the metal ring 4 has only a uniform inner circumferential surface denoted with reference numeral 10 from which the phase 9 comes away.

With the cross-sectional configuration previously discussed and shown in the figure, the metal ring 4 made of zinc has a total mass equal to the mass of the stainless steel ring conventionally used.

The metal ring 4 at its outer circumferential surface forms oppositely disposed grooves 11, extending in the axial direction and during assembly cooperating with projections 12 that are formed on the coupling member 1. The metal ring 4 is held in a circumferentially extending circumferential groove 13 of the coupling member 1 in the axial direction in which the radially outer portion of the metal ring 4 engages (see FIG. 5).

LIST OF REFERENCE NUMERALS 1 coupling member
2 fastening foot
3 recess
4 metal ring
5 flange region
6 pin section
7 ring surface
8 ring region
9 phase
10 inner circumferential surface
11 groove
12 protrusion
13 circumferential groove
14 driveshaft
16 switch
20 brushhead assembly
21 coupling assembly
24 arm portion
26 brush member
28 ring
30 proximal end
34 spring member

The invention claimed is:

1. A brush head attachment for an electric sonic toothbrush, comprising a shank member carrying a bristle bundle, and a coupling member provided on a fastening-side end of said shank member with at least one connection surface for a drive shaft of a handpiece which, when said brush head attachment is mounted on said handpiece, protrudes into said coupling member, a spring element that can be operatively connected with said drive shaft for securing said drive shaft to said brush head attachment and/or transferring a drive motion of said drive shaft to said brush head attachment, and a metal ring disposed in a widened fastening foot formed by said coupling member, wherein said metal ring is a die-cast member, and wherein said metal ring at its outer circumferential surface comprises grooves formed opposite to each other and extending in an axial direction.

2. The brush head attachment according to claim 1, wherein said metal ring is a die-cast member made of zinc.

3. The brush head attachment according to claim 1, wherein said metal ring forms a flange region from which a pin section extending into said coupling member projects away, and from which a ring surface projects at the opposite side, the outer diameter of which is smaller than the outer diameter of said metal ring.

4. The brush head attachment according to claim 3, wherein said ring surface changes via a phase to a uniform cylindrical inner circumferential surface of said metal ring.

5. A brush head attachment for an electric sonic toothbrush, comprising a shank member carrying a bristle bundle, and a coupling member provided on a fastening-side end of said shank member with at least one connection surface for a drive shaft of a handpiece which, when said brush head attachment is mounted on said handpiece, protrudes into said coupling member, a spring element that can be operatively connected with said drive shaft for securing said drive shaft to said brush head attachment and/or transferring a drive motion of said drive shaft to said brush head attachment, and a metal ring disposed in a widened fastening foot formed by said coupling member, wherein said metal ring is a die-cast member made of zinc forming a flange region from which a pin section extending into said coupling member projects away, and from which a ring surface projects at the opposite side, the outer diameter of which is smaller than the outer diameter of said metal ring, wherein said ring surface changes via a phase to a uniform cylindrical inner circumferential surface of said metal ring.

6. The brush head attachment according to claim 5, wherein said metal ring at its outer circumferential surface comprises grooves formed opposite to each other and extending in an axial direction.

7. A brush head attachment for an electric sonic toothbrush, comprising a shank member carrying a bristle bundle, and a coupling member provided on a fastening-side end of said shank member with at least one connection surface for a drive shaft of a handpiece which, when said brush head attachment is mounted on said handpiece, protrudes into said coupling member, a spring element that can be operatively connected with said drive shaft for securing said drive shaft to said brush head attachment and/or transferring a drive motion of said drive shaft to said brush head attachment, and a metal ring disposed in a widened fastening foot formed by said coupling member, wherein said metal ring is a die-cast member, wherein said metal ring—forms a flange region from which a pin section extending into said coupling member projects away, and from which a ring surface projects at the opposite side, the outer diameter of which is smaller than the outer diameter of said metal ring, and wherein said ring surface changes via a phase to a uniform cylindrical inner circumferential surface of said metal ring.

* * * * *

UNITED STATES PATENT AND TRADEMARK OFFICE
CERTIFICATE OF CORRECTION

PATENT NO. : 9,237,943 B2  
APPLICATION NO. : 14/035578  
DATED : January 19, 2016  
INVENTOR(S) : Arndt Graeve Page 1 of 1

It is certified that error appears in the above-identified patent and that said Letters Patent is hereby corrected as shown below:

In the Claims

Column 6, Line 13, Claim 7, delete "ring-forms" and insert -- ring forms --

Signed and Sealed this  
Thirty-first Day of May, 2016

Michelle K. Lee  
*Director of the United States Patent and Trademark Office*